United States Patent [19]
Burbaum et al.

[11] Patent Number: 5,876,946
[45] Date of Patent: Mar. 2, 1999

[54] HIGH-THROUGHPUT ASSAY

[75] Inventors: Jonathan J. Burbaum, Cranbury, N.J.; Thomas D.Y. Chung, Wilmington, Del.; Gregory L. Kirk, Skillman; James Inglese, Dayton, both of N.J.; Daniel Chelsky, Moylan, Pa.

[73] Assignee: Pharmacopeia, Inc., Princeton, N.J.

[21] Appl. No.: 868,280

[22] Filed: Jun. 3, 1997

[51] Int. Cl.[6] .................................................. G01N 33/53
[52] U.S. Cl. ........................... 435/7.1; 435/7.2; 435/7.71; 435/7.72; 435/7.9; 435/7.92; 435/7.93; 436/501; 436/518; 436/531; 436/534; 250/261.2
[58] Field of Search ................................. 435/5, 7.1, 7.2, 435/7.71, 7.72, 7.8, 7.91, 7.93, 240.1, 240.3, 240.24, 240.25; 436/501, 518, 531, 534, 537; 250/261.2

[56] References Cited

U.S. PATENT DOCUMENTS

| | | |
|---|---|---|
| 4,568,649 | 2/1986 | Bertoglio-Matte . |
| 5,032,720 | 7/1991 | White . |
| 5,091,652 | 2/1992 | Mathies et al. . |
| 5,114,477 | 5/1992 | Mort et al. . |
| 5,120,953 | 6/1992 | Harris . |
| 5,162,941 | 11/1992 | Favro et al. . |
| 5,210,636 | 5/1993 | Baer . |
| 5,260,578 | 11/1993 | Bliton et al. . |
| 5,274,240 | 12/1993 | Mathies et al. . |
| 5,283,684 | 2/1994 | Thomas et al. . |
| 5,304,810 | 4/1994 | Amos . |
| 5,313,079 | 5/1994 | Brasen et al. . |
| 5,323,079 | 6/1994 | Nieves et al. . |
| 5,334,870 | 8/1994 | Katada et al. . |
| 5,351,152 | 9/1994 | Kuo et al. . |
| 5,547,849 | 8/1996 | Baer et al. . |
| 5,556,764 | 9/1996 | Sizto et al. . |

FOREIGN PATENT DOCUMENTS 0 681 477 A1 11/1995 European Pat. Off. .

OTHER PUBLICATIONS

Molecular Devices, Fluorescent Imaging Plate Reader, the Premier Optical Screening Instrument, 4 pages.

Dietz et al., Volumetric Capillary Cytometry: A New Method for Absolute Cell Enumeration, Cytometry 23:177–186 (1996).

Quesada et al., Chemosensitization and drug accumulation assays as complementary methods for the screening of multidrug resistance reversal agents, Cancer Letters 99 (1996) 109–114.

Manz et al., In situ identification of Legionellaceae using 16S rRNA–targeted oligonucleotide probes and confocal laser scanning microscopy, Microbiology (1995), 141, 29–39.

Michael Hanley, Peptide Binding Assays, Neurotransmitters Receptor Binding, 2nd edition, 1985, pp. 91–102.

Schroeder et al., FLIPR: A New Instrument for Accurate, High Throughput Optical Screening, Journal of Biomolecular Screening, vol. 1, No. 2, 1996, pp. 75–80.

Cuatrecasas et al., Membrane Receptors and Hormone Aciton, Advances in Protein Chemistry 30,251–451 (1976).

Ted Dixon, Random mask brightens image, Nature, vol. 383, Oct. 31, 1996, pp. 760–761.

Sales Brochure, IMAGN 2000, 4 pages.

Morrow et al. "Synthetic Peptides from a Conserved Region of the HIV Envelope Induce Broadly Reactive Anti–HIV Responses" International Conference on AIDS, vol. 6, No. 1 (1990), meeting abstract, p. 207 (Abstract No. Th.A.350).

*Primary Examiner*—Jeffrey Stucker
*Attorney, Agent, or Firm*—Darby & Darby

[57] ABSTRACT

A homogeneous high throughput assay is described which screens compounds for enzyme inhibition, or receptor or other target binding. Inhibition (or binding) by the library compounds causes a change in the amount of an optically detectable label that is bound to suspendable cells or solid supports. The amounts of label bound to individual cells or solid supports are microscopically determined, and compared with the amount of label that is not bound to individual cells or solid supports. The degree of inhibition or binding is determined using this data. Confocal microscopy, and subsequent data analysis, allow the assay to be carried out without any separation step, and provide for high throughput screening of very small assay volumes using very small amounts of test compound.

38 Claims, 6 Drawing Sheets

HIGH-THROUGHPUT ASSAY

FIELD OF THE INVENTION

This invention relates to the high throughput screening of chemical compounds for interactions with target molecules.

BACKGROUND OF THE INVENTION

To find lead compounds for drug discovery programs, large numbers of compounds are often screened for their activity as enzyme inhibitors or receptor agonists/antagonists. Large libraries of compounds are needed for such screening. As a result of developments in this field, it is now possible to simultaneously produce combinatorial libraries containing hundreds of thousands of small molecules for screening. With the availability such libraries, however, has come a need for large scale, rapid screening methods.

For example, the libraries may be contained on microbeads, each compound being present in a picomolar amount. Because the amount of compound is very small, it is advantageous to conduct the high throughput screening method in very small volumes, e.g., on the order of 1 μl. Such assays can be performed in the 1536 well plate described in U.S. patent application Ser. No. 60/037,636 filed Feb. 18, 1997. Microassays in such small volumes, however, are difficult to accurately and repeatedly perform using conventional methods.

Receptor binding assays used in high throughput screening typically involve three steps. First, a labelled ligand is incubated with a target receptor in the presence of compound to be tested for inhibition of ligand/receptor binding. Second, the receptor and ligand (and compound) are separated using filtration and/or washing of an immobilized receptor. Finally, the amount of labelled ligand bound to the receptor is quantified. This conventional screening is a 'separations-mode' assay, i.e., one in which the bound ligand is physically separated from the free ligand using either a filtration membrane or the selective adhesion of either bound or free component to a surface (e.g., the surface of a microtiter plate).

Separation, however, is time-consuming and therefore slows high throughput screening. It can also, if fluid handling steps employed are not sufficiently precise, create variations in the signal generated in the assay and can disturb equilibrium binding conditions. Furthermore, separation is difficult to automate and is potentially hazardous when radioactive materials are involved. These problems are particularly acute in assays conducted in microvolumes using small amounts of test compound.

It is therefore advantageous in high throughput screening to distinguish bound and free ligands in a homogeneous assay, i.e., one that eliminates the need for separation. To be particularly useful in screening large scale combinatorial libraries, such an assay should readily permit small volumes, and small amounts of test compounds, to be used.

A homogeneous assay is described in U.S. Pat. No. 4,568,649 which employs beads that are impregnated with a scintillant (these are commercially sold as Scintillation Proximity Assay beads (SPA™, Amersham Corp., Arlington Heights, Ill.)). The beads are also coated with a ligand that is capable of binding with radio-labelled target in a sample. When the ligand binds to the radio-labelled target, the scintillant on the bead is activated by the radiolabel. The level of light energy produced by the scintillant indicates the amount of bound labelled target in the sample. This method, however, requires handling of radioactive reagents and is somewhat limited in sensitivity.

Another homogeneous assay is known in which signal is generated when labeled ligand and labeled target interact. One label is an energy donating Eu-cryptate having a long-lived fluorescent excited state and the other is an energy-accepting protein, allophycocyanin, having a short fluorescent excited state. Energy transfer occurs between the labels when they are less than 7 nm apart. During the assay, the Eu-cryptate is excited by a pulsed laser, and its fluorescent emission continually re-excites the allophycocyanin, whose fluorescence is measured by a time resolved fluorescence reader. This method, however, requires labeling of both the ligand and the target and is not as sensitive as some other commercially available assays. Also, allophycocyanin is a very large, multimeric protein which can affect the assay in an unpredictable manner.

A fluorescent imaging plate reader has been used to perform optical screening in cell-based kinetic assays that measure membrane potential and intracellular calcium. The assay employs an optical method that limits the depth of field measured by a CCD camera to the bottom of an assay well, where fluorescence in a layer of live adherent cells is measured. By limiting the depth of field to the cell layer, background fluorescence from extracellular dye is reduced. Data is obtained over time measuring, e.g., depolarization of cells (Schroeder et al., (1996) *Journal of Biomolecular Screening* 1:75–80). This method, however, uses live cells that require maintenance for the period of the assay, necessitating complicated integrated fluid handling to trigger rapid cellular events. Such handling is very difficult, if not impossible, to perform in the microvolumes that are used in high throughput screening of small amounts of library compounds. Also, measurement is taken of a bulk sample, i.e., of the entire layer of cells and the assay does not discriminate between fluorescence bound to individual suspended cells and background fluorescence.

It is therefore an object of the present invention to provide an assay for high throughput screening that does not require a separation step, i.e., is homogeneous.

It is another object of the invention to avoid radioactive waste, and to avoid labeling of both ligand and target molecule.

It is another object of the invention to provide an assay which is readily adaptable for miniaturization in microvolumes, and which is highly sensitive.

It is another object of the invention to provide a high throughput screening method for detecting activity of small amounts of compounds, such as are found in combinatorial libraries of beads having picomolar amounts of compound thereon.

SUMMARY OF THE INVENTION

The present invention relates to a high throughput assay for rapidly screening a plurality of compounds. The assay determines the degree of inhibition by the compounds of a ligand/receptor interaction, or of an enzyme catalyzed reaction, or the degree of binding of library compounds to a target molecule. Inhibition (or binding) by the library compounds causes a change in the amount of an optically detectable label that is bound either to suspendable cells or to suspendable solid supports. The degree of inhibition (or binding) is determined by measuring, by microscopy, the amounts of label that are bound to individual cells or solid supports. These amounts are compared with the amount of label that is not bound to individual cells or solid supports (i.e., background signal). The degree of inhibition or binding is determined using this data. Preferably, measurement is performed using a confocal microscope. The assay is homogeneous, i.e., no separation step is required to remove unbound label, since the amount of bound label is distinguished by scanning of the individual cells or solid supports. The method allows exceptional sensitivity and high throughput to be obtained in assays using small volumes, and small amounts of test compound.

DETAILED DESCRIPTION OF THE INVENTION

All patent applications, publications, or other references that are listed herein are hereby incorporated by reference.

The present invention allows high throughput screening of compounds, such as those found in combinatorial libraries, to determine active drug candidates. The method allows substantial reduction in the time required for screening such libraries over that required by non-heterogeneous methods. It also eliminates the need for disposal of washed reactants and is highly adaptable to performance in microvolume assay vessels. In addition, the method improves over conventional homogeneous assay methods in its higher signal to noise ratio and in requiring use of only one label. It provides a sensitive assay that allows successful screening of very small amounts of compounds derived from microbead libraries, thereby allowing more assays using those microbeads, and faster, more efficient screening.

The method of the invention involves measurement of the amounts of bound and free signal in the assay by microscopy. This can be carried out, for example, by sequentially viewing different depths in the sample using a conventional microscope employing a narrow depth of focus. According to the preferred method of the invention, however, confocal microscopy is employed to individually determine the amount of bound signal to individual cell sized particles.

Confocal microscopy confines detection of an illuminated object, or sample, to a thin object plane. A view of a "slice" of the object, or sample, is obtained. This is achieved, for example, by placing a spacial filter, such as a pinhole, in the image plane located between the objective lens and a detector. Only light emitted from a narrow region near the object plane converges through the spacial filter. Light from other planes is blocked by the filter. Images are obtained of the object plane, e.g., by scanning, in sequence, the points in the field of view, to obtain the "slice".

Confocal microscopy using laser scanning is particularly preferred for use in the invention. A suitable laser scanning microscope is sold as "IMAGN/2000" by Biometric Imaging Inc. (Mountain View, Calif.). Laser scanning microscopes are also described in U.S. Pat. Nos. 5,556,764 and 5,547,849. These microscopes are conventionally used to analyze blood within a capillary tube to determine the number of cells labelled by fluorescent antibodies.

Non-laser scanning confocal microscopes are well known and can also be used to practice the invention. For example, confocal microscopes using spinning Nipkow disks, or similar arrangements can be used, if desired. Such microscopes are described, e.g., in Dixon (1996) Nature, 383:760; Juskaitis et al. (1996) Nature 383:804; Petran et al. (1968) J. Opt. Soc. Am. 58, 661; and Xiao et al. (1988) Appl Phys. Lett. 53:716.

Useful confocal microscopes are also described, for example, in U.S. Pat. Nos. 5,032,720; 5,120,953; 5,260,578; 5,304,810; 5,283,684; 5,351,152, and 5,162,946.

According to the method of the invention, data obtained by confocal microscopy are analyzed to determine the difference between signal associated with individual suspended cells or solid supports, and background signal, and to obtain a measure of inhibition or binding. Conventional confocal microscopy for, e.g., counting CD4+ cells, is not concerned with this determination, or with high throughput screening of compounds.

Any desired optically detectable label can be used in the present invention, including fluorescent labels and chemiluminescent labels. If the label is chemiluminescent, it is preferred that it generate a short-lived signal. Enzymes that produce a visible color change in the presence of appropriate substrate, such as horse radish peroxidase and alkaline phosphatase, can also be used. Fluorescent labels are referred and are described below with respect to preferred embodiments of the invention. Other optically detectable labels, however, may be substituted in these embodiments if desired.

In one embodiment, the assay screens compounds for inhibition of binding of a fluorescently labeled ligand to a target molecule contained on the surface of either suspendable cells or solid supports. The degree of binding inhibition is determined by measuring, through confocal microscopy, amounts of labeled ligand bound to individual cells or supports in the presence of the compounds.

In this embodiment, a suspended cell-membrane bound receptor can be contacted with fluorescently labelled ligand, in the presence of library compounds to be screened for inhibition of receptor binding. (The term "receptor" is used herein to encompass receptor domains as well as whole receptors.) As an example, a library of compounds to be screened for inhibition of the binding of IL-8 to its cell surface receptor is contacted with a suspension of cells bearing the receptor in the presence of fluorescently labelled IL-8. When examined by confocal microscopy, cells bound to labeled IL-8 appear as regions of increased fluorescence on a background of relatively constant "free" label. The amount of cell associated fluorescence is less in an assay where active compound inhibits binding of ligand to receptor.

This embodiment is schematically depicted in FIG. 1. FIGS. 1A and 1C show a cell with attached receptors ('Y'), as they bind to fluorescently-labelled ligands (solid square flagged with 'F'). In FIG. 1C, fluorescently-labelled ligands are displaced by library compound (open triangles). FIGS. 1B and 1D schematically indicate fluorescence collected from sections of samples with and without active library compounds, respectively. Presence of a "spot" relative to background fluorescence indicates bound ligand, while the background fluorescence itself results from free ligand. Confocal microscopy allows measurement of individual cell-sized "spots" of bound fluorescence. The amount of free fluorescent ligand can be simultaneously determined. In FIG. 1B, the cells are significantly more fluorescent than the background and therefore show up as more intense spots. In FIG. 1D, the effect of displacement by an active library compound is illustrated. The same cells have become dimmer or indistinguishable from background as a consequence of ligand displacement. Thus, the loss of 'bound' signal indicates an active molecule in a high-throughput screening assay. Since receptor binding assays are typically conducted with an excess of ligand, the amount of background fluorescence does not normally change.

In the assay of the invention, the amount of fluorescence associated with individual cells (or solid supports) in the assay is totaled. This total provides a measure of the amount of binding between ligand and target. This amount is compared to the amount of free fluorescence to arrive at a value indicative of the activity of the library compound (the amount may increase or decrease for active drug candidates, depending on the way in which the assay is set up). Specific methodologies for arriving at particular values indicating binding (or inhibition of binding) are described below. While background fluorescence can be individually measured in each assay, this may not be necessary where the background fluorescence is relatively constant.

The method of the invention is particularly advantageous in increasing the level of signal to background noise. By eliminating signal from label contained in solution outside of the "slice" containing the measured particles or cells, the background noise is significantly reduced. The ratio of signal to background noise was found to be about fifteen times lower in a commercially available conventional heterogeneous (i.e., separation-based) assay using $^{125}$I labeled ligand than in the method of the invention.

The method is especially effective in measuring fluorescence for samples that have been allowed to settle. Confocal microscopy allows accurate measurement of a "slice" or "section" of liquid in a container. Thus, measurement can be taken of, e.g., the bottom 10% of the sample where fluorescence bound to the cells or solid particles is concentrated. This is not possible in prior art assays using conventional optical detection since such assays do not eliminate signal from the volume above the settled cells or solid particles. Elimination of this signal accounts, in part, for the very high signal to noise ratio achieved by the method of the invention.

Preferably, the suspended cells (or suspended solid supports) are allowed to settle for about 10 minutes or more, so that more than about 75% of the cells or supports are contained in less than about 25% of the volume of the assay container, i.e., a cell or solid support layer forms on the bottom. Most preferably, more than 90% of the cells or supports are allowed to settle in less than about 10% of the volume of the container. In one preferred embodiment, the thickness of the layer of cells or supports is about the same as the thickness of the confocal object plane. The time required for settling is a function of column height, and so is higher, e.g., for samples in 96 well plates than for samples in 1536 well plates.

Any desired combination of ligand and receptor can be employed in the assay of the invention to test for active inhibitors. Non-limiting examples of ligands and their cell based receptors include neurokinin and NK2R cells, and IL-8 and IL-8B/CHO cells. These receptors and ligands are discussed further in the Examples below.

Other examples of ligands and receptors include, but are not limited to, insulin/insulin receptor, bradykinin/bradykinin receptor, erythropoietin/EPO receptor, and leptin/Ob receptor. Cell lines for performing these assays are available. For example, IM-9 (ATCC CCL-159) constitutively expresses human insulin receptor. IMR-90 (ATCC CRL 7931) constitutively expresses bradykinin B2 receptor and can be stimulated with interleukin-1δ to produce bradykinin B1 receptor. Cells that express EPO receptor are described by Kitamura et al., *J. Cellular Physiology* 140:323–334 (1989). Cells expressing leptin receptor (i.e., OB receptor) are described by Tartaglia et al., *Cell* 83:1263–1271 (1995).

Figure 1A:
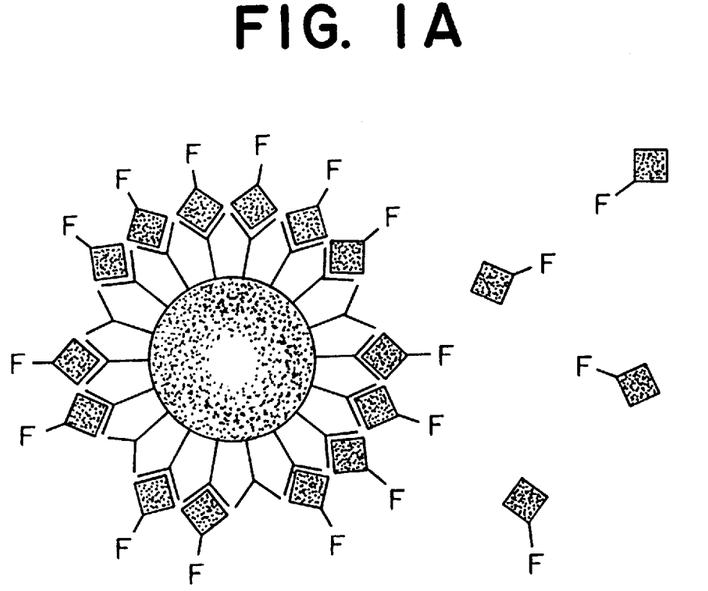
FIGS. 1A–1D are schematic depictions of an embodiment of the present invention employing a suspension of cells having surface receptors that bind to fluorescently labelled ligand. Active library compounds inhibit cell-bound fluorescence, causing a decrease in signal that is measured for individual cells.
Figure 1B:
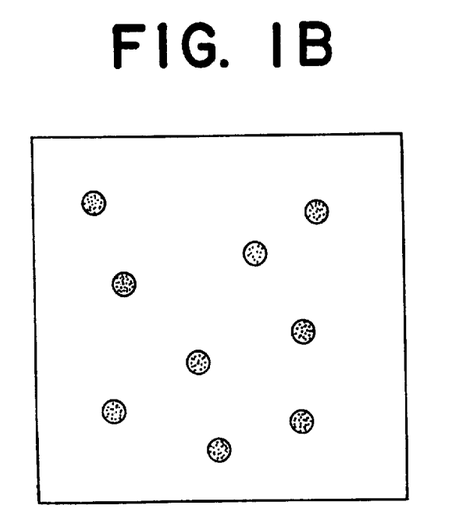
Figure 1C:
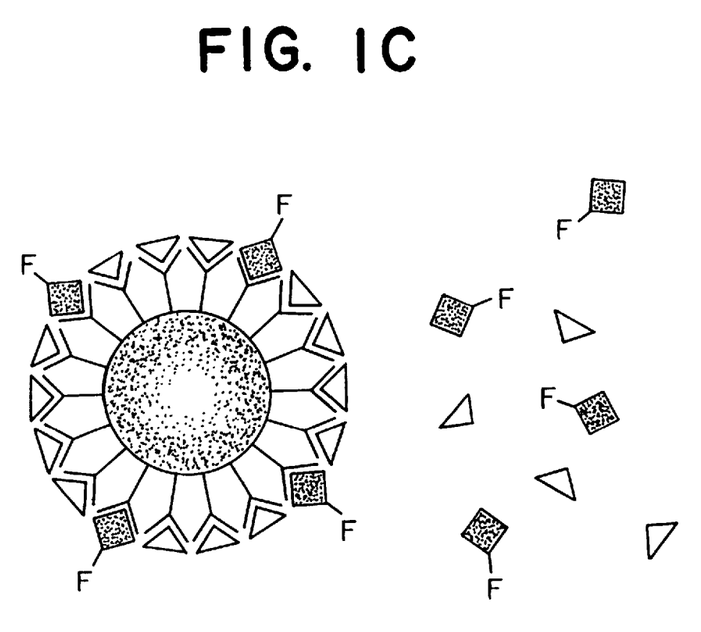
Figure 1D:
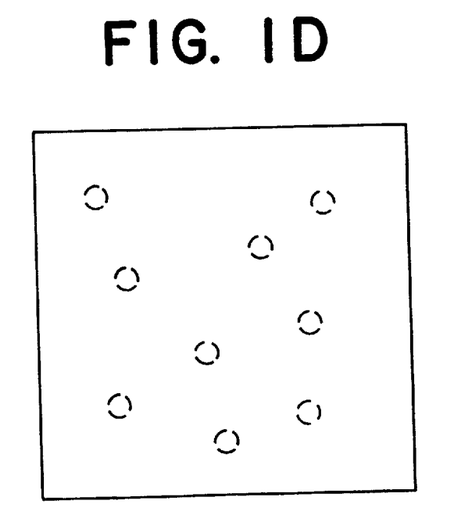
Figure 2:
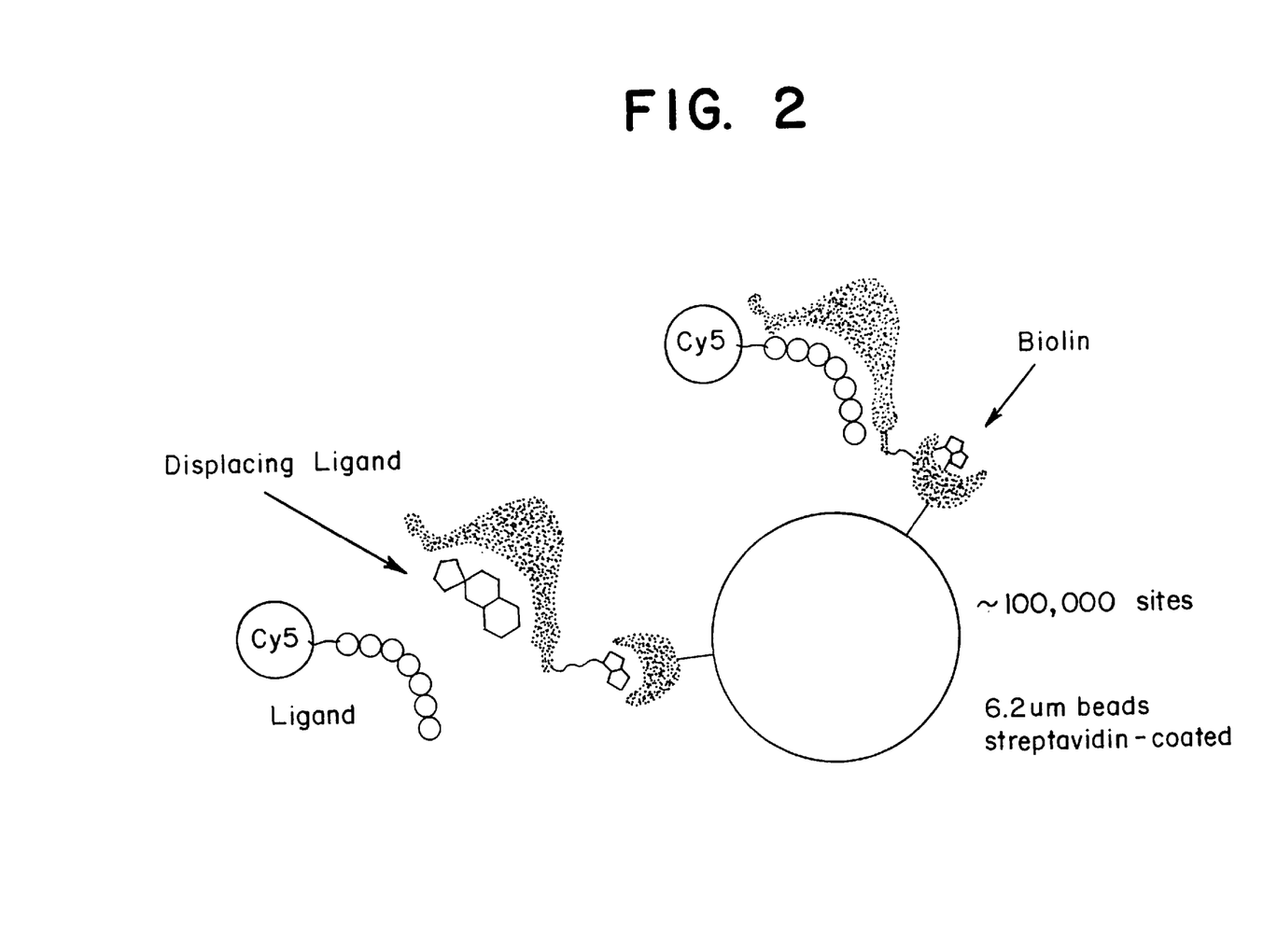
FIG. 2 is a schematic depiction of an embodiment of the present invention employing beads having target molecules coated thereon that bind to fluorescently labelled ligand in the assay medium unless an active library compound is present.

In another embodiment of the invention, a target molecule is bound, e.g. via a biotin/avidin association, to suspendable solid supports, and library compound and fluorescently labeled ligand in solution are contacted with the supports. Active compound causes a decrease in support-associated fluorescence by displacing fluorescent ligand from the target, and the presence and/or potency of the test compound is quantitated. The brightness of fluorescence of the supports diminishes in proportion to the potency of the test compound. This method is schematically depicted in FIG. 2.

"Suspendable solid support" is intended to refer to any solid support capable of being suspended in a liquid. The support should be small enough so it does not block optical access to the rest of the solution upon settling to the bottom of the assay well. On the other hand, the support should be large enough so that it does not remain in suspension for an extended period of time after the assay components are combined. The preferred supports are less than about 50 μm in diameter, most preferably less than 10 μm in diameter. The diameter of the supports is preferably less than, although not significantly less than, the thickness of the confocal object plane. The supports are preferably greater than 1 μm in diameter, so that the suspension does not require centrifugation to condense the supports to the bottom of the assay container.

A preferred suspendable support is a 6.2 μm bead made of polystyrene and commercially available from Spherotech (Libertyville, Ill.). Such beads are avidin coated, typically containing $10^6$ binding sites per bead. Any suitable suspendable solid support, however, can be employed, including cellulose beads, controlled pore-glass beads, silica gels, and other types of polystyrene beads (optionally cross-linked with divinylbenzene and optionally grafted with polyethylene glycol and optionally functionalized with amino, hydroxy, carboxyl, or halo groups). Additional supports include grafted co-poly beads, poly-acrylamide beads, latex beads, dimethylacrylamide beads (optionally cross-linked with N,N$^1$-bis-acryloyl ethylene diamine), glass particles coated with hydrophobic polymers, etc., (i.e., having a rigid or semi-rigid surface). Divinylbenzene-crosslinked, polyethyleneglycol-grafted polystyrene type beads can be used, such as TentaGel S-NH$_2$® beads (Rapp Polymere, Tubingen, Germany).

The solid support can be coated with any desired target, including, but not limited to, hydrolases (including proteases, esterases, nucleases), ligases (DNA or RNA based) and transpeptidases, as well as binding proteins such as antibodies, and DNA-binding proteins, and domains of those proteins.

The target (or ligand) coated on the solid support may be bound thereto by any desired means. It may, for example, be biotinylated and then non-covalently linked to a streptavidin coated support. It is also possible to bind the target (or ligand) to antibodies (which are specific for the target) that have been coated on the support. Covalent linkages are also known in the art.

The support may also be coated with a recombinantly produced receptor, or receptor binding domain. This is particularly advantageous for receptors or domains that are not normally expressed on the cell surface. For example, nuclear receptors, such as steroid receptors, are advantageously expressed recombinantly, and employed in the microbead assay of the invention. One such receptor is human recombinant estrogen receptor (Alexis Biochemicals, San Diego, Calif.). For a cell surface receptor, however, it is preferred to use suspended cells expressing the receptor as opposed to beads having the receptor bound thereto.

It is also possible, for example, to coat the suspendable solid supports with ligand, and perform the assay of the invention with labelled receptor in solution, in the presence of compounds to be screened for inhibition of ligand/receptor binding.

It is also possible, according to the invention, to incubate fluorescently labelled library compounds in solution with suspended cells or solid supports, and measure the binding between said compounds and cells or supports in the absence of ligand. In other words, the assay provides a direct measure of binding between the compounds and target molecule on the cells or supports, without the need to add a ligand that is displaced by the compounds.

In another embodiment, a library of compounds is assayed for inhibition of an enzyme catalyzed reaction and the amounts of fluorescence bound to individual suspendable solid supports measured to determine the degree of inhibition. For example, in one such assay, the amount of fluorescence bound to a microbead in the presence of inhibitory compounds is greater than for non-inhibitory compounds. The amounts of fluorescence bound to individual beads are determined by confocal microscopy. Using this type of assay, inhibition can be determined of a protease, such as cathepsin D, which cleaves fluorescently labelled substrate bound to the solid support. For cathepsin D, the substrate can be a peptide, e.g. lys-pro-ile-glu-phe-phe-arg-leu, linked at one end to the microbead and at the other end to the fluorescent label Cy-5; either linkage can be accomplished using a spacer such as gamma aminobutyric acid.

It is also possible, using this type of assay, to determine inhibition of endonuclease cleavage of fluorescently labelled oligonucleotide. The endonuclease is placed in solution with library compound and suspendable solid supports that are coated with fluorescently labelled oligonucleotide substrate. Upon cleavage of the substrate, fluorescently labeled product is released from the supports. The amount of fluorescence that remains bound to the bead increases where active inhibitor is present.

In another assay for enzyme inhibition, both enzyme and fluorescently labelled substrate are incubated in solution with test compound and microbeads coated with a ligand. The ligand (such as an antibody) specifically binds to the reaction product of the enzyme catalyzed reaction, the reaction product retaining the fluorescent label. For example, inhibitors of tyrosine kinase can be determined in an assay in which kinase and fluorescently labelled peptide substrate are in solution. The peptide substrate contains a tyrosine amino acid in the middle of its sequence, and the reaction product contains phosphotyrosine. The assay solution contains suspendable microbeads coated with antibody for the phosphotyrosine containing reaction product. Successful inhibition by a library compound results in a decrease in fluorescence bound to beads as compared with controls.

In assays of the invention in which inhibition of an enzyme catalyzed reaction is determined, the inhibitory compounds can inhibit by any mechanism. For example, they can inhibit by binding to enzyme, binding to substrate, binding to a complex of enzyme and substrate, or binding to a complex of enzyme and product.

Preferably, the assay of the invention is performed using a microtiter plate having microvolume containers, such as the 1536 well plate described in U.S. patent application Ser. No. 60/037,636 filed Feb. 18, 1997. A confocal scanning microscope sequentially scans the bottom of each well in the microtiter plate.

The method can also be carried out in conventional 96 well microtiter plates, or in any other container or on any surface capable of holding liquid samples and of being scanned by a confocal microscope. Examples include 12-well, 24-well, 384-well, 864-well plates, and microscope-slides.

In the embodiment of the invention in which receptor-bearing cells are employed, the desired density of cells will preferably be between about 100 and 1000 cells per microliter in a 1536 well plate and between about 30 to 300 cells per microliter in a conventional 96 well plate. Typically, it is believed necessary to measure signals from at least 100 to 1000 cells per sample to obtain a statistically relevant result. The optimum density can be determined using these concentrations as a guideline, as well as the size of the particular cells employed, and by measuring the signal provided in assays using known inhibitors of the ligand/receptor interaction. The area scanned can be limited to reduce scanning time and thereby increase throughput, as long as the number of cells measured is sufficient.

If suspendable supports are employed in the preferred size of about 6 $\mu$m, the preferred density of supports will generally be in the same preferred range as for cells. The density varies depending on the size of the supports and the amount of target affixed to each support.

The signal detected according to the invention, is preferably generated by a fluorescent label. The label can be attached to a ligand which binds to a receptor or other target molecule. It is also possible to use labelled receptor (or other target molecule) in certain embodiments of the invention. Also, if desired, a "secondary labelling" approach can be used in which labelled antibody probes, e.g., for unlabelled ligand, receptor, or target molecule.

It is also possible to conduct an assay according to the invention in which library compounds themselves are fluorescently labelled. For example, a library of compounds that are primary amines can be labelled with an amine-specific fluorescent label (e.g., monofunctional Cy5-NHS ester). The compounds can then be tested for direct binding to a target molecule on a cell or suspended support. The amount of bound fluorescence correlates to the degree of binding.

Fluorescent labels suitable for use in the invention are well known and include cyanine dyes such as Cy-5, Cy-5.5, and Cy7 (Amersham Corp.), fluorescein, rhodamine and Texas red. In the embodiment of the invention employing cells, it is preferred that the fluorescent label fluoresce at a relatively high wavelength, i.e., higher than about 450 nm, to avoid interference from cell originating fluorescence and fluorescence originating from glass and plastic containers. The labels most preferably fluoresce above 600 nm, and at less than about 800 mn. Labels that excite at about 400 nm can avoid photobleaching caused by near-UV light.

Non-fluorescent labels can also be used in embodiments of the invention described above. In one embodiment using the chemiluminescence generating label luciferase, a receptor is coated on suspendable solid supports. The coated supports are incubated with luciferase conjugated ligand, luciferase substrate, and compound to be tested. In the absence of inhibition of receptor/ligand binding, the luciferase becomes associated with the suspendable solid supports, and the chemiluminescent signal that results from luciferase's enzymatic action concentrates around the supports. In the presence of inhibitory compounds, the signal associated with the supports decreases.

In a separate embodiment of the invention, the assay is performed to determine the degree of binding to a treated surface of an insuspendable solid support. The support can be a container, or vessel, itself, such as the bottom of a microtiter plate. Alternately, the insuspendable support can be, e.g., a disc. In the embodiment in which the support is the bottom of the well of the microtiter plate, the plate is coated with a target molecule, and then exposed to labelled ligand. A confocal section including the bottom layer of the plate is measured for optically detectable signal. Free signal is measured in other confocal sections that do not include the bottom of a microtiter plate. The signal bound to the support can then be calculated. This method is advantageous in that scanning can be rapidly performed. Individual cells/beads do not need to be identified, resulting in higher throughput. Use of a thin confocal object plane is preferred to exclude signal emanating from above the coated plate, and to maintain a high signal to noise ratio. In one embodiment of this method, the confocal object plane is less than about 10 $\mu$m.

It is preferred that the compounds assayed in the high throughput method of the invention be derived from combinatorial libraries on polymer beads. By synthesizing sufficient compound on each bead for a few assays, compound handling is reduced or eliminated. Such beads, e.g., can contain on the order of 100 picomoles of compound per bead, and tests are often performed at concentrations of about 1 $\mu$M. With such beads, a test volume of 1 $\mu$l is advantageous since it is possible to use one bead for up to about one hundred tests.

Preferably, the library compounds are eluted from the beads and evaporated to dryness in microtiter plates in preparation for the assay. Compounds on beads can be released by photocleavage, or another type of cleavage. Cleavage of photocleavable linkers is preferred. Such linkers, and methods for their cleavage, are described in Barany et al. (1985) *J. Am. Chem. Soc.* 107:4936. Examples of other linkers and the relevant cleavage reagents are described in WO 94/08051.

Using combinatorial libraries prepared on beads, the identity of active compounds is preferably determined using the encoding system described in WO 94/08051, and in U.S. patent applications Ser. Nos. 08/436,120 and 08/239,302 (which correspond to WO 95/30642). In this system, chemical tags encoding the identities of the compounds are applied to the solid supports. The identity of the compound on a given support can be determined by detaching the chemical tags from the support, identifying the tags by, e.g., gas chromatography, and correlating the identities of tags with the identity of the compound. Once an active compound is identified, the corresponding bead (which had contained the compound) can be examined, and the identity of the compound determined by releasing the tags and decoding by this method.

When several large libraries are available for testing, it may be advantageous to "scout" each library by placing more than one test compound in each assay container. Assay containers having an active compound can be further investigated by individually evaluating each of the plurality of compounds present in such containers. Screening at "high density" in this manner allows one to statistically evaluate the number and potency of active compounds in each library. Libraries which contain the most active compounds can be more thoroughly tested. If the proportion of active compounds screened in the assay is high, a second assay of the active compounds may be performed at lower concentrations to select only the most active compounds to choose those that should be further evaluated.

The invention is illustrated by the following examples, which are not intended to limit the scope of the invention.

EXAMPLE 1

Screening of Compounds for Receptor Binding

The invention was demonstrated using confocal microscopy apparatus and software originally intended for fluorescent cytometry. The data obtained were further analyzed to provide values indicative of the amount of binding between ligand and a cell surface receptor.

1) Synthesis of Ligands (a) Cy5-labelled Neurokinin-A (NKA).

Neurokinin-A (HKTDSFVGLM) was purchased from Cambridge Research Biochemicals (PP-05-0826A), and monofunctional Cy5 dye was purchased from Amersham (as the Fluorolink™ conjugation kit, cat. # A25001). NKA (1 mg) was dissolved in 0.88 mL bicarbonate buffer (100 mM NaHCO$_3$, pH 9.3), and Cy5 dye (about 1 mg) was dissolved in 0.13 mL bicarbonate buffer. The two solutions were mixed and incubated for 1.5 hr at room temperature, then transferred to 5° C. for an additional 17 hrs. The conjugate was purified by HPLC (gradient 20–40% CH$_3$CN in H$_2$O, 0.1% TFA, on a Vydac® analytical C18 column, R$_t$8.9 min @ 1.5 mL/min) to yield 157 mol (18% theoretical yield). Identity of the ligand was verified by competition vs. receptor and mass spectrometry.

(b) Cy5-labelled IL-8.

Human interleukin-8, Ser72→Cys mutant (hIL-8(S72C)) was cloned from human cDNA using PCR techniques and sequenced to confirm the mutation and the sequence. Monofunctional Cy5-iodoacetamide was obtained from Amersham. To 500 nM Cy5-iodoacetamide was added 200 nmol (200 $\mu$l of a 1 mM stock) of hIL-8(S72C) in 20 mM sodium phosphate, pH 6.5, 400 mM NaCl. The tube was vortexed and placed in the dark at ambient temperature. HPLC analysis indicated that after 48 hours the reaction was complete. The product was purified (2×100 $\mu$l injections) from unreacted Cy5-iodoacetamide and oxidized hIL-8 (S72C) by HPLC. Sample was reconstituted in 50 mM sodium phosphate, pH 7.2 at an estimated concentration of 400 $\mu$M. A more accurate concentration was then determined from a fluorescence spectrum of an aliquot of this sample. Further characterization indicated that hIL(S72C)-Cy5 had a mobility similar to wild type IL-8 on a 16% SDS-PAGE analysis and displayed a K$_i$ of 2 nM in a conventional [$^{125}$I]IL-8 ligand displacement assay.

2) Cell lines (a) Cells expressing neurokinin-2 receptor (NK2R/CHO) were obtained. Cells expressing NK2R are well known, and readily obtained by those skilled in the art. For example, NK2R expressing cells are described in the following references: Arkinstall, S., M. Edgerton, et al. (1995). "Co-expression of the neurokinin NK2 receptor and G-protein components in the fission yeast Schizosaccharomyces pombe." *FEBS Lett* 375(3): 183–7; Bradshaw, C. G., K. Ceszkowski, et al. (1994). "Synthesis and characterization of selective fluorescent ligands for the neurokinin NK2 receptor." *J Med Chem* 37(13): 1991–5; Grisshammer, R., J. Little, et al. (1994). "Expression of rat NK-2 (neurokinin A) receptor in *E. coli.*" *Receptors Channels* 2(4): 295–302; Lundstrom, K., A. Mills, et al. (1995). "High-level expression of G protein-coupled receptors with the aid of the Semliki Forest virus expression system." *J Recept Signal Transduct Res* 15(1–4): 617–30; and Turcatti, G., K. Nemeth, et al. (1996). "Probing the structure and function of the tachykinin neurokinin-2 receptor through biosynthetic incorporation of fluorescent amino acids at specific sites." *J Biol Chem* 271(33): 19991–8.

b) Cells expressing IL-8A and IL-8B receptor (IL-8A/CHO and IL-:8B/CHO) were obtained as follows:

CHO IL-8A and IL-8B cell lines were prepared by cationic lipopolyamine (lipofectamine, GIBCO BRL) mediated transfection of CHO-K1 cells (ATCC) with pCDNAIII plasmids encoding the sequences of human IL-8A or IL-8B. Cells were cultured under G418 selection (1 mg/ml) in DMEM, 10% fetal bovine serum, 2 mM L-glutamine, and 2% non-essential amino acids and clonal lines expressing the highest receptor levels were maintained for use in these experiments. The human IL-8A receptor cDNA was cloned from HL-60 cell (ATCC) mRNA. (Clones encoding IL-8A are described in Ahuja et al., (1992) *Nature Genetics* 2:31.) First-strand cDNA was synthesized using M-MLV reverse transcriptase (Promega Riboclone™ cDNA synthesis system) and IL-8A cDNA was amplified by polymerase chain reaction using primers, 5'CCGAAT-TCGACATGTCAAATATTACAGATCC3' and 5'GCTCTAGATCAGAGGTTGGAAGAGAC3'. The PCR product was digested with EcoRI+Xbal and ligated into EcoRI/Xbal/calf intestinal phosphatase-digested pcDNA3 vector (Invitrogen). The DNA sequence of one candidate was confirmed using the Promega Silver Sequence™ method. To generate the human IL-8B expression clone, an approximately 1.8 kb cDNA fragment was recloned from pBluescript clone BS-p3 (Murphy and Tiffany, (1991) *Science,* 253:1280) into the pcDNA3 vector, using EcoRI and Xhol.

3) Assay (a) Binding of Cy5-NKA to NK2R/CHO cells

A culture of NK2R/CHO cells, near confluence, was washed with 12 mL DPBS($Mg^{+2}$ & $Ca^{+2}$ free), trypsinized by adding trypsin (2 mL/T-25 flask), incubating at 37° C. for about 5 min, then quenching with 10 mL media. Cells were then counted, and diluted to the desired final concentration of cells (5,000 cells/25 µL). The assay was set up with the following components: Buffer (1× BSS+0.2% BSA, containing thiorphan and bacitracin) containing varying concentrations of Cy5-NKA (0.76 to 136 nM final) 10 µL; Cells, 40 µL. The plate was covered and wrapped in aluminum foil to protect from light and left to shake for 1 hr at room temperature. For each sample, 25 µL was removed, placed in an IMAGN 2000™ capillary, and read using IMAGN™ software (Biometric Imaging, Inc.) The sample was allowed to settle until the cells rested on the bottom of the well. The time require for settling was typically 10 minutes.

(b) Displacement of Cy5-NKA bound to NK2R/CHO cells by SR48,968.

SR-48,968 is a known inhibitor of the binding of NKA neurokinin 2 receptor. Setup and assay were performed as in (a), at a fixed concentration of Cy5-NKA of 5 µM, and diluting stock concentration of SR-48,968 (stock 1 mM, 1.6% DMSO, in BSS) from 88 nM to 8.8 pM in Cy5-NKA-containing buffer.

(c) Displacement of Cy5-IL-8 bound to cells by unlabelled IL-8.

A culture of IL-8B/CHO cells, near confluence, was trypsinized by adding trypsin (2 mL/T-25 flask), incubating at 37° C. for about 1 min, then quenching with 4 mL media. Cells were then counted, and diluted to the desired final concentration (15,000 cells/25 µL). The assay was set up in a 96-well microliter plate (100 µL total volume), consisting of the following components: Buffer (1× BSS) 30 µL; Cells, 25 µL; Background fluor (Tris-Cy5, 60 µM), 25 µL; hIL-8 (S72C)-Cy5(20 nM), 10µL; unlabelled IL-8 (various concentrations, diluted in BSS), 10 µL. The plate was covered and wrapped in aluminum foil to protect from light and left to shake for 1 hr at room temperature. For each sample, 85 µL was removed and placed in an IMAGN 2000™ capillary, and read using IMAGN software.

4) Data Analysis

The data that results from the IMAGN system consists of a tab delimited text file that contains information about each cell that has been identified in the field. The IMAGN system provides position, shape, and intensity data (for two channels, Cy5 and Cy5.5) for each cell (or cell-sized object) in the imaging field, as well as baseline information. (In a typical analysis using this type of equipment, cells are identified by two or more contiguous pixels having intensities significantly greater than the baseline signal.) Statistical parameters (e.g., standard deviations) of the data are also tabulated. This data can be analyzed to give a scalar value for the sample which provides a measure of the amount of binding. Three possible ways to perform this further analysis are described below.

(a) Mean Fluorescence Intensity.

This value is derived from the data table as the mean value across all cells of "MaMO". Channel 0 (zero) is the Cy5 fluorescence channel, and the MaMO value is calculated as the peak Cy5 fluorescence (corresponding to fluorescence bound to the cell) with the minimum (baseline fluorescence) value subtracted out. "MaMO" is tabulated for each cell in the field.

This analysis is particularly useful for assays that involve high fluor concentrations and relatively high levels of occupation of cell surface receptors. It may not be advantageous where all cells cannot be detected, e.g., at low fluor concentrations or low levels of occupation of cell surface receptors. Analysis of F value (explained below) can provide more accurate data under these circumstances. Specifically, more weakly fluorescent cells (by virtue of their size and/or idiosyncratic binding characteristics) will 'disappear' first in the imaging field when being displaced by a competing ligand. ("Disappearance", in this sense, means that the pixels comprising the cell's image are not significantly higher in intensity than the baseline image.) Two changes are observed experimentally when challenging a fixed fluorescent ligand concentration with a competitor. First, the overall intensity of the cells decreases (i.e., the average MaMO value decreases). Second, the number of observable cells decreases, since the weaker cells vanish into the background. The F-value measures the total fluorescence in the cell layer and therefore provides a more accurate measurement when all cells cannot be counted.

(b) F-value.

The F-value is determined by multiplying the MFI by the total number of cells loaded into the well (as opposed to the number of fluorescent cells counted), and dividing by 1000. This value provides the total fluorescence of the cell layer, and includes cells whose fluorescence is so weak as to be undetectable in a given scan by the confocal microscope. The F-value is believed to generally provide a more accurate measure of binding in a given sample.

(c) Percent of Control.

Percent of control analysis can be performed using values obtained from either an MFI or F-value analysis, and results in normalization of this data. It is calculated according to the following formula for the relevant value. "Max" and "min" refer to the maximum and minimum fluorescence for the relevant value.

$$\% \text{ Control} = ((\text{Value} - \text{Min}) / (\text{Max} - \text{Min})) \times 100$$

Figure 3:
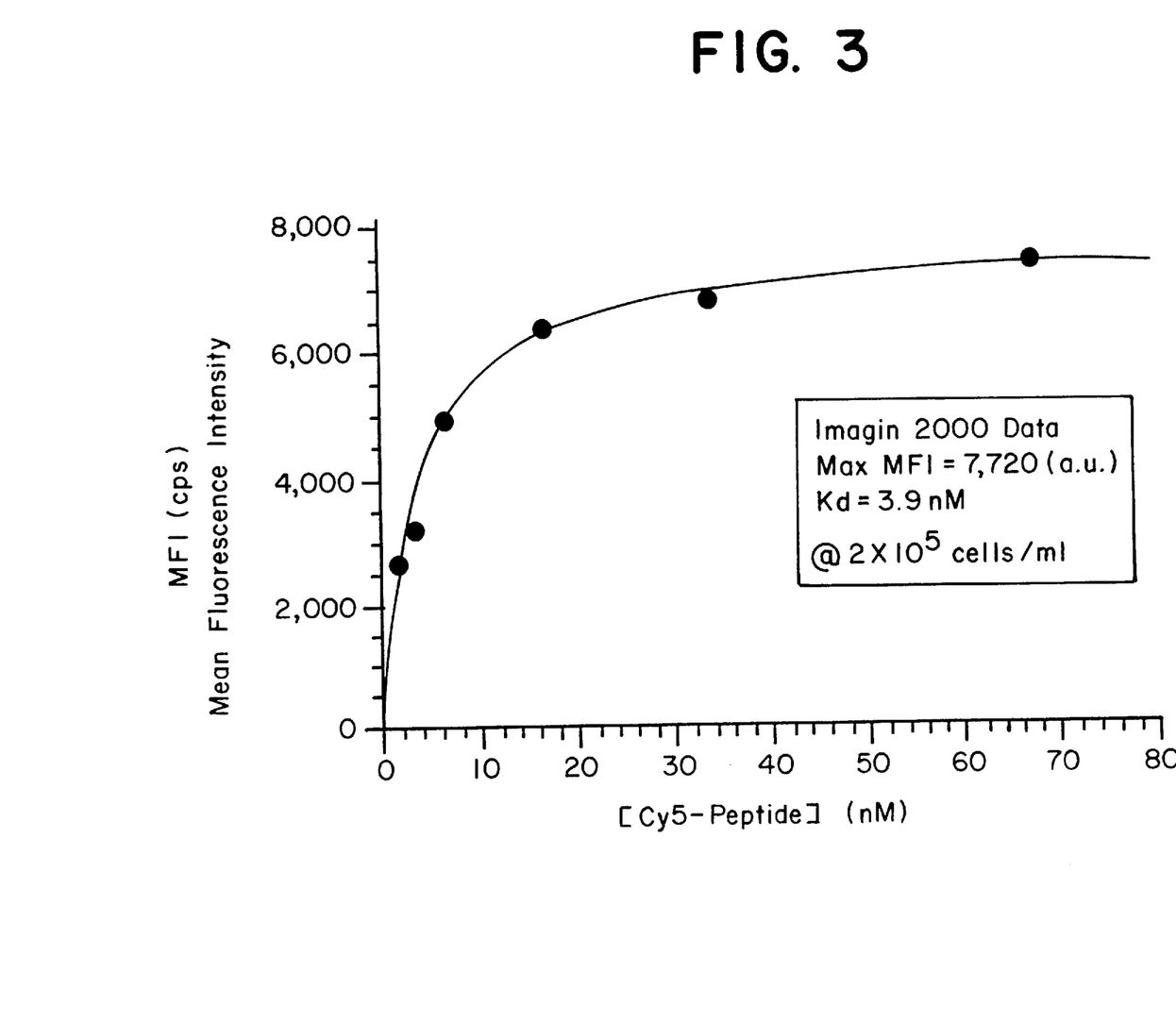
FIG. 3 is a graph showing the mean fluorescent intensity (MFI) calculated for binding of Cy5-NKA to NK2R/CHO cells.

The MFI calculated for binding of Cy5-NKA to NK2R/CHO cells is shown in FIG. 3. These results show a maximum MFI of 7,720 and a Kd (dissociation constant) of 3.9 nM.

Figure 4:
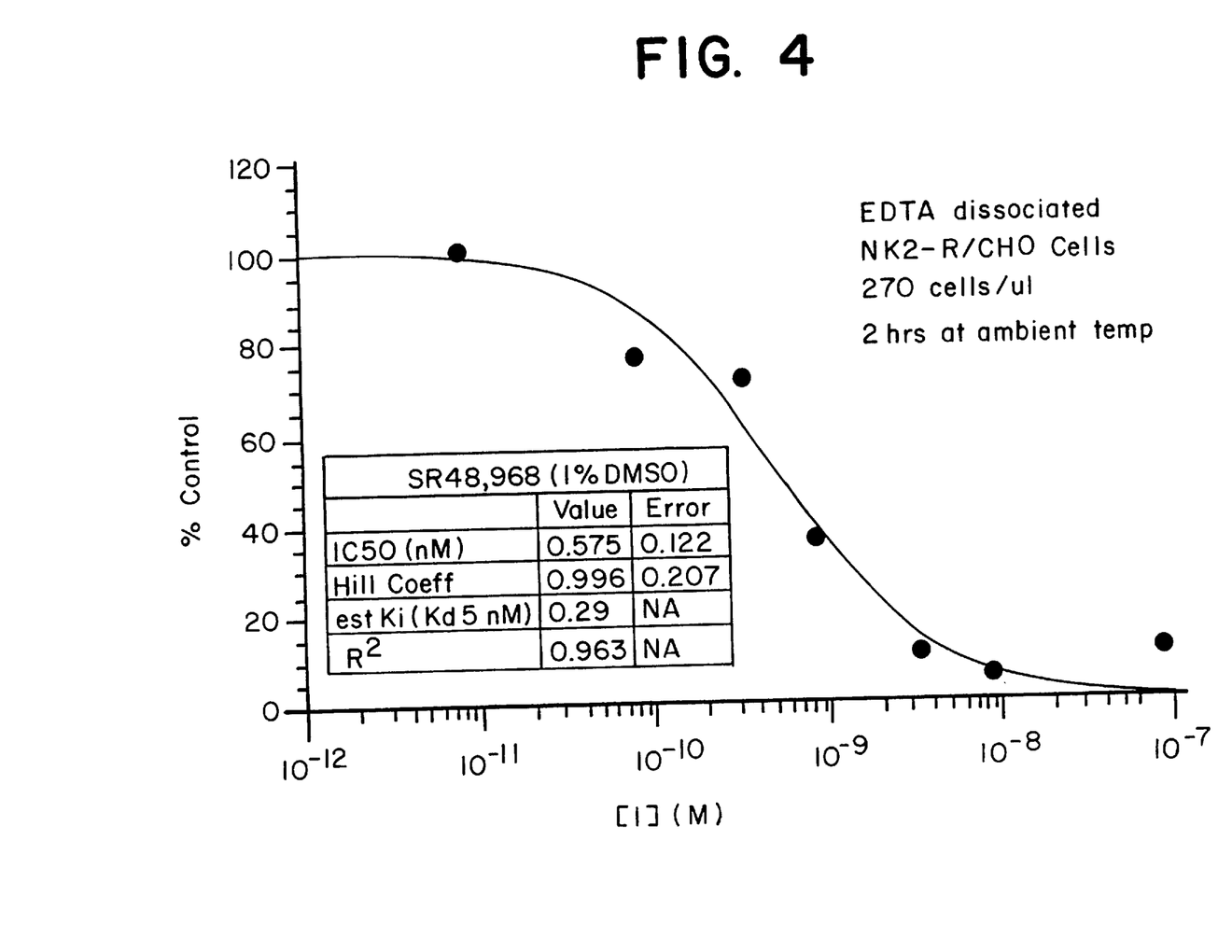
FIG. 4 is a graph showing fluorescence associated with cells calculated as percent of control for displacement of Cy5-NKA by SR48.968.

Results calculated as a percent of control for displacement of Cy5-NKA by SR48.968 are shown in FIG. 4. An $IC_{50}$ of 0.575 nM was determined and an estimated Ki of 0.29 nM. An $R^2$ value of 0.963 was determined, indicating "goodness of fit" of the experimental data to the theoretically determined values.

The Hill coefficient measured was 0.996. The Hill coefficient is a measure of the cooperativity in binding. For a simple system, where one receptor binds to one ligand, the Hill coefficient is 1. For polyvalent systems, the Hill coefficient can vary from one, but ideally is a small integer for polyvalent ligands, or the reciprocal of a small integer for polyvalent receptors. The NKA/NK2R and IL-8/IL-8BR systems involve monovalent receptors and monovalent ligands.

Figure 5:
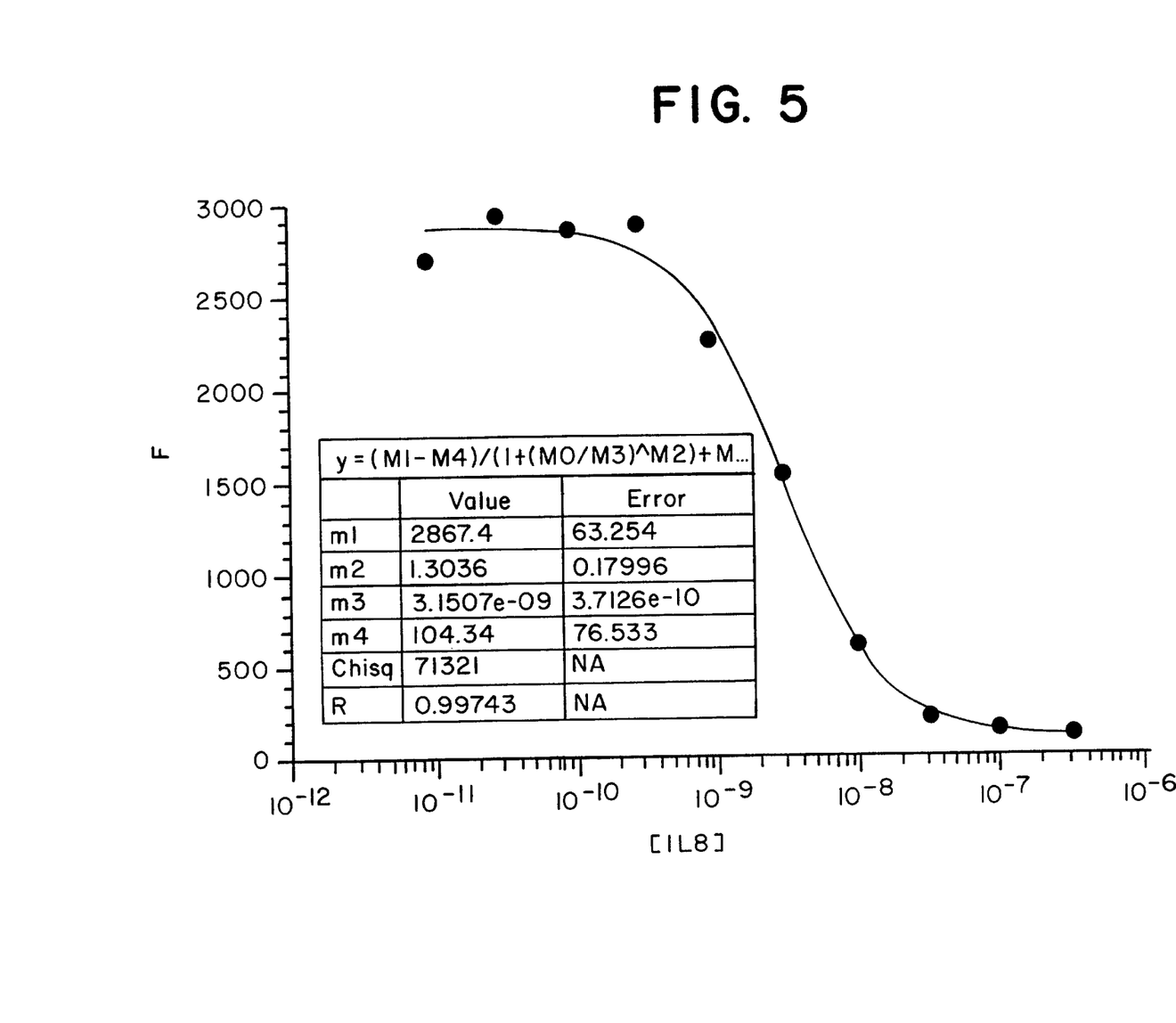
FIG. 5 is a graph of F-values obtained for displacement of fluorescently labelled IL-8 by unlabeled IL-8.

Results, calculated as F-values, for displacement of labelled IL-8 by unlabelled IL-8, are shown in FIG. 5. The graph insert provides the equation for a four-parameter curve fit:

$$y = ((M1 - M4) / (1 + (M0/M3)^{M2})) + M4.$$

where M is the maximum value, M4 is the minimum value, M3 is the midpoint of the curve (the apparent Kd), and M2 is the slope at the midpoint.

Binding constants for the above results can be determined, by Scatchard analysis, which involves the measurement of bound ligand as a function of free ligand concentration. Specifically, the ratio of bound to free ligand is plotted versus the bound ligand concentration. A straight line results, whose slope is the negative reciprocal of the dissociation constant for the ligand, and whose x-intercept is the maximum binding value ($B_{max}$).

The results of these experiments demonstrate that the method of the invention allows precise quantitative analysis of ligand/target binding, and can be used for a variety of targets commonly employed in combinatorial library screening. The method also allows rapid detection and analysis in high-throughput screening. The variablity in the results is low and the results strongly correlate with those obtained by conventional methods of analysis. The method is easily performed in a microscopic volume. It is therefore well-suited for high-throughput screening in microliter samples, such as when using a 1536-well plate, and allows efficient use of small amounts of library compounds derived from coated microbeads.

5) Comparison with conventional assay.

In receptor binding assays, the sensitivity of the assay is limited by background. It is possible to compare sensitivities of different assays by calculating the ratios of maximum signal to background. For the assay described above involving IL-8 binding, the assay of the invention was found to provide a signal (F-value) of 6300 on a non-specific background of 200, for a signal-to-background ratio of 31.5. For example, [$^{125}$I]IL-8 binding analysis using a similar concentration of labelled IL-8 results in a signal of 85,000 cpm on a non-specific background of 39,000 cpm, for a signal-to-background ratio of 2.1. Based on these values, the improvement in sensitivity is about 15-fold using the assay of the invention.

EXAMPLE 2

Screening of compounds for SH2 domain binding

A high-throughout assay is performed to determine inhibitors of binding of ligand to the SH2-domain of human Grb2. Grb2 is an adaptor protein, the SH2-domain of which binds to phosphotyrosine containing proteins and promotes signal transduction by causing the association of specific cellular proteins. Cloning of Grb2 is described in Lowenstein et al., *Cell* 70:431–442 (1992). IRS-1 is a substrate for the insulin receptor (IR) tyrosine kinase, and binds to the SH2 domain of Grb2 after being tyrosine phosphorylated. (The interaction of IRS-1 with Grb2 is described in Skolnick et al., *EMBO* 12:1929–1936 (1993).)

Preferred ligands for this assay have a dissociation constant of less than about 1 $\mu$M. The present assay employs a synthetic ligand for the SH2-domain that is a phosphotyrosine containing peptide derived from the sequence of IRS-1 (located near the pY896 amino acid). The peptide has the sequence KSPGNpYVNIE-$CO_2NH_2$.

Streptavidin coated 6.2 $\mu$m beads (Spherotech) are employed that contain $1 \times 10^6$ binding sites per bead. The beads are incubated with the SH2-domain (Src-homology 2 domain), which has been labelled at a specific site with biotin during expression (Schatz, P. J. (1993) Bio/Technology 11, 1138–1143).

Beads, ligand, and library compounds are combined, incubated and shaken in 1536 well plates. The samples are then allowed to settle for about 10 minutes, and the plates read by a laser scanning confocal microscope. Active compounds cause a decrease in the amount of bound fluorescence. Results are analyzed as described above in Example 1 to determine binding and/or inhibition constants.

EXAMPLE 3

Screening of compounds for EGF Receptor Kinase Domain binding

A high throughput assay is performed to determine library compounds that inhibit binding of ligand to the kinase domain of the epidermal growth factor (EGF). This kinase phosphorylates a number of proteins and peptides, including the peptide RRKGSTAENAEYLRVA (the "1173" peptide). The tyrosine underlined in the amino acid sequence is phosphorylated by the kinase.

EGF Receptor Kinase Domain is obtained from Alexis Biochemicals (San Diego, Calif.). The 1173 peptide is biotinylated and then incubated with streptavidin coated 6.2 μKm microbeads (Spherotech) to affix the peptide to the beads. Monoclonal antibodies specific for phosphotyrosine are obtained from Sigma (St. Louis, Mo.) or Biogenesis (Sandown, N.H.), and are labelled with Cy5 following the manufacturer's directions (Amersham).

The assay is conducted in 1536 well plates. The EGF kinase domain is incubated in the presence of the 1173 coated microbeads, Mg●ATP, Cy5 labelled antiphosphotyrosine antibody, and library compound in neutral buffer. Upon phosphorylation of the 1173 peptide by the kinase, the peptide is bound by the fluorescently labelled antibody, and fluorescence becomes associated with the beads. Inhibitory library compound prevents phosphorylation, resulting in a decrease in bead associated fluorescence. The wells of the plate are scanned by a laser scanning confocal microscope, and the resulting data further analysed as described in Example 1 to determine inhibition and/or binding values.

We claim:

1. A high throughput assay for rapidly screening a plurality of compounds to determine the degree of inhibition of a ligand/receptor interaction or of an enzyme catalyzed reaction by said compounds, or to determine the degree of binding of said compounds to a target molecule, said assay comprising:
   (a) a step selected from the group consisting of
      (1) contacting said compounds to be tested with said ligand and said receptor;
      (2) contacting said compounds to be tested with said enzyme and substrate for said enzyme; and
      (3) contacting said compounds to be tested with said target molecule;
   wherein inhibition or binding by one or more of said compounds causes a change in the amount of an optically detectable label bound to suspendable cells or solid supports present in said assay;
   (b) determining said degree of inhibition or binding by: measuring through use of confocal microscopy amounts of said optically detectable signal bound to individual cells or solid supports; comparing said amounts with an amount of back-ground signal in said assay that is not bound to said cells or solid supports; and determining said degree of inhibition or binding from the difference between said bound and background signal,
   wherein said assay is homogeneous.

2. The assay of claim 1 comprising an assay for enzyme inhibitors.

3. The assay of claim 1 comprising an assay for inhibitors of receptor binding.

4. The assay of claim 3 wherein said receptor consists of a receptor domain that binds to said ligand.

5. The assay of claim 1 wherein said optically detectable label is selected from the group consisting of a chemiluminescent label, a fluorescent label, and an enzyme that produces a visible color change.

6. The assay of claim 1 wherein said ligand is fluorescently labelled.

7. The assay of claim 1 wherein said library compounds are fluorescently labelled.

8. The assay of claim 2 comprising an assay wherein enzyme and library compound in solution are incubated with fluorescently labelled substrate that is attached to suspendable solid supports, said incubation resulting in release of fluorescently labelled reaction product in the absence of inhibitory compound.

9. The assay of claim 2 wherein enzyme and fluorescently labelled substrate are incubated with suspendable solid supports that are coated with a moiety that specifically binds to the reaction product of said enzyme/substrate reaction, and wherein said reaction product is fluorescently labelled.

10. The assay of claim 1 wherein said receptor is labelled and said ligand is bound to said suspendable solid supports.

11. The assay of claim 1 wherein said confocal microscopy is laser scanning confocal microscopy.

12. The assay of claim 1 wherein said confocal microscopy employs a Nipkow disc.

13. The assay of claim 1 wherein said compounds are contacted with enzyme and substrate, and inhibit by a mechanism selected from the group consisting of binding to said enzyme, binding to said substrate, binding to a complex of enzyme and substrate, and binding to a complex of enzyme and product.

14. The assay of claim 1 wherein prior to step (b) said suspendable cells or solid supports are allowed to settle in containers in which said assay is conducted such that more than about 75% of said cells or solid supports are settled in less than about 25% of the volume of said containers.

15. A high throughput assay for rapidly screening a plurality of compounds for inhibition of binding of a fluorescently labeled ligand to a target molecule contained on suspendable cells or solid supports, said method comprising
   (a) contacting said fluorescently labeled ligand with said target molecule contained on said suspendable cells or suspendable solid supports in the presence of said compounds;
   (b) measuring the degree of inhibition of said binding by determining through use of confocal microscopy amounts of fluorescently labeled ligand bound to individual cells or solid supports;
   (c) comparing said amounts with fluorescence in said assay that is not associated with said cells or solid supports, and
   (d) correlating said difference with said degree of inhibition, wherein said assay is homogeneous.

16. The method of claim 15 wherein said target molecule is a receptor or receptor domain.

17. The method of claim 16 wherein said receptor or receptor domain is contained on the surface of suspended cells.

18. The method of claim 15 wherein said target molecule is attached to a suspendable solid support.

19. The method of claim 18 wherein said suspendable solid support is less than about 50 μm in diameter.

20. The method of claim 18 wherein said suspendable solid support is less than about 10 μm in diameter and more than about 1 μm in diameter.

21. The assay of claim 15 wherein prior to step (b) said suspendable cells or solid supports are allowed to settle in containers in which said assay is conducted such that more than about 75% of said cells or solid supports are settled in less than about 25% of the volume of said containers.

22. The assay of claim 15 wherein said confocal microscopy is laser scanning confocal microscopy.

23. A homogeneous assay for screening a library of compounds for inhibition of binding between a ligand and a cell surface receptor or receptor domain comprising:
   a) adding a liquid suspension of cells expressing said cell surface receptor or domain to a plurality of containers;
   b) adding a library of compounds to be screened for said inhibition to said plurality of containers;
   c) adding a fluorescently labelled ligand for said receptor to said containers;

d) incubating said cells, said compounds, and said fluorescently labelled ligand;

e) individually measuring amounts of fluorescence associated with said cells in said containers by confocal microscopy; and f) determining the degree of inhibition by one or more of said compounds of binding of said ligand to said receptor.

24. The method of claim 23 wherein, following said incubation and prior to said measurement, said cells are allowed to settle in said containers such that more than about 75% of said cells are settled in less than about 25% of the volume of said containers.

25. The method of claim 23 wherein, following said incubation and prior to said measurement, said cells are allowed to settle in said containers such that more than about 90% of said cells are settled in less than about 10% of the volume of said containers.

26. The method of claim 23 wherein said compounds are fluorescently labelled with a moiety that fluoresces at a wavelength above about 600 nm.

27. The method of claim 23 wherein said containers comprise wells in one or more microtiter plates.

28. The method of claim 23 wherein said containers comprise about 1 μl or less of assay solution.

29. The assay of claim 23 wherein said confocal microscopy is laser scanning confocal microscopy.

30. A homogeneous assay for screening a library of compounds for inhibition of binding between a ligand and a target molecule attached to a suspendable solid support comprising:

a) adding a liquid suspension of said target molecules attached to said suspendable solid supports to a plurality of containers;

b) adding a plurality of compounds to be screened for said inhibition to said plurality of containers;

c) adding fluorescently labelled ligand to said containers;

d) incubating said target molecules attached to solid supports, said compounds, and said fluorescently labelled ligand;

e) individually measuring amounts of fluorescence associated with said solid supports by confocal microscopy; and f) determining the degree of inhibition by one or more of said compounds of binding of said ligand to said target molecule.

31. The method of claim 30 wherein, following said incubation and prior to said measurement, said solid supports are allowed to settle in said containers such that more than about 75% of said cells are settled in less than about 25% of the volume of said containers.

32. The method of claim 30 wherein, following said incubation and prior to said measurement, said solid supports are allowed to settle in said containers such that more than about 90% of said cells are settled in less than about 10% of the volume of said containers.

33. The method of claim 30 wherein said compounds are fluorescently labelled with a moiety that fluoresces at above about 600 nm.

34. The method of claim 30 wherein said containers comprise wells in one or more microtiter plates.

35. The method of claim 30 wherein said containers comprise about 1 μl or less of assay solution.

36. The assay of claim 30 wherein said confocal microscopy is laser scanning confocal microscopy.

37. A homogeneous assay for screening a library of compounds for inhibition of binding between a ligand and a target moiety attached to an insuspendable solid support or cells comprising:

a) adding a plurality of compounds to be screened for said inhibition to containers comprising said insuspendable solid support or cells;

b) adding fluorescently labelled ligand to said containers;

c) incubating said target moiety attached to said insuspendable solid support or cells, said compounds, and said fluorescently labelled ligand;

d) measuring the amount of fluorescence associated with said solid support or cells by confocal microscopy; and e) determining the degree of inhibition by one or more of said compounds of binding of said ligand to said target moiety.

38. The assay of claim 37 wherein said containers comprise wells of a microtiter plate, and said insuspendable solid support comprises the bottom of wells in said plate.

* * * * *